United States Patent [19]

Mazid et al.

[11] Patent Number: 5,059,535

[45] Date of Patent: Oct. 22, 1991

[54] PROCESS FOR THE SEPARATION AND PURIFICATION OF SIALYL TRANSFERASES

[75] Inventors: M. Abdul Mazid; Mohammed A. Kashem, both of Edmonton, Canada

[73] Assignee: Chembiomed, Ltd., Edmonton, Canada

[21] Appl. No.: 336,932

[22] Filed: Apr. 12, 1989

[51] Int. Cl.$^5$ .............................................. C12N 9/10
[52] U.S. Cl. ................................. 435/193; 435/175; 435/280; 435/803; 435/815
[58] Field of Search ............... 435/193, 175, 280, 815, 435/803

[56] References Cited

U.S. PATENT DOCUMENTS

| | | | |
|---|---|---|---|
| 4,250,262 | 2/1981 | Taubman et al. | 435/193 |
| 4,560,661 | 12/1985 | Katsumata et al. | 435/195 |
| 4,704,361 | 11/1987 | Miccoli et al. | 435/194 |
| 4,925,796 | 5/1990 | Bergh et al. | 435/193 |

OTHER PUBLICATIONS

Weinstein et al., *J. Biol. Chem.* (1987) 262(36):17735–17743.
Gross et al., *Eur. J. Biochem.* (1987) 168:595.
De Heij et al., *J. Carbohydrate Chem.* (1988) 7(1):209–222.
David et al., *Pure & Appl. Chem.* (1987) 59(11):1501–1508.
Beyer et al., *Adv. in Enzymol.* (1981) 52:23–175.
Barker et al., *Methods Enzymol.* (1974) 34:479–491.
Joziasse et al., *J. Biol. Chem.* (1985) 260(8):4941–4951.
Weinstein et al., *J. Biol. Chem.* (1982) 257(22):13835–13844.
Conradt et al., "*Sialic Acids*" (1988) Proceedings of the Japanese–German Symposium, Berlin, p. 104.
Sadler et al., *J. Biol. Chem.* (1979) 254(11):4434–4443.
Sadler et al., *J. Biol. Chem.* (1979) 254(13):5934–5941.
Higa et al., *J. Biol Chem.* (1985) 260(15):8838–8849.
Paulson et al., *J. Biol. Chem.* (1977) 252(7):2356–2362.
Sticher et al., *Biochem. J.* (1988) 253:577–580.
Elices et al., *Arch. Biochem. Biophys.* (1987) 254(1):329–341.
Paulsen, J. C. et al., *J. Biol Chem.* (1982) 257(8):4034–4037.

*Primary Examiner*—Herbert J. Lilling
*Attorney, Agent, or Firm*—Kate H. Murashige

[57] ABSTRACT

Specific sialyl transferases (ST) are important enzymes in the manufacture of carbohydrate moieties useful for pharmacological purposes and for diagnostic and clinical procedures. The invention offers simplified methods to isolate highly specific forms of these ST enzymes by taking advantage of the affinity of the ST for its acceptor substrate in the presence of the sialyl-CMP analogs, such as CDP. Specifically exemplified are isolation of the alpha 2,3-ST, specific for Le$^c$ or LacNAc, and alpha 2,6-ST specific for LacNAc.

9 Claims, 4 Drawing Sheets

PROCESS FOR THE SEPARATION AND PURIFICATION OF SIALYL TRANSFERASES

TECHNICAL FIELD

The invention is directed to methods of separating various specificities of sialyl transferases (ST). Specifically, the invention concerns a method to specifically adsorb ST enzymes using supports derivatized to acceptors appropriate to the relevant ST in the presence of substrate analogs, such as cytidine diphosphate (CDP).

BACKGROUND ART

Sialyl transferases are important enzymes for use in the preparation of pharmaceutical compounds and as diagnostic and clinical reagents for specifically reacting carbohydrates. All sialyl transferases (ST) catalyze the general reaction:

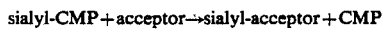

sialyl-CMP + acceptor → sialyl-acceptor + CMP

There are a large number of ST enzymes distinguished on the basis of the type of linkage formed (e.g., alpha-2,3 or alpha-2,6) and on the acceptors for which they are specific. It has been estimated that 10–12 specific STs are required to synthesize all of the sialylated structures in mammalian systems. (Paulson, J. C. et al. *J Biol Chem* (1987) 262:17735–17743.)

Purified forms of specific ST enzymes are useful both as research tools and as synthetic reagents for the manufacture of pharmaceuticals (Gross, H. J. et al. *Eur J Biochem* (1987) 168:595). For example, these enzymes have been used in the regiospecific and stereospecific synthesis of disialylated tetrasaccharides analogous to M and N blood group determinants of glycophorin A (DeHeij, H. T. et al. *J Carbohydrate Chem* (1988) 7:209–222). The necessity for purified enzymes in order to produce desired sialylated oligosaccharides was pointed out by, for example, David, et al. *Pure Appl Chem* (1987) 59:1501–1508.

Because of the recognized need for purified forms of the specific STs, various approaches have been made to purification of these enzymes from natural sources, especially those with the highest concentrations of STs, such as liver, platelets and erythrocytes. A general discussion of such purification procedures is found in Beyer, T. A. et al. *Adv Enzymol* (1981) 52:23–175, and the desirability of affinity purification is recognized. Most commonly used affinity ligands have been purine and pyrimidine nucleotides linked to solid supports through spacer arms (Barker, R. et al. *Methods Enzymol* (1974) 34:479–491. This type of affinity ligand is not only expensive, but has proved unsatisfactory in use.

Purification of various specific ST enzymes has been reported by a number of groups, as follows:

Joziasse, et al. *J Biol Chem* (1985) 260:4941 report the purification of alpha 2,3-ST from human placenta;

Heij, et al. *J Carbohydrate Chem* (1988) 7:209–222 have reported purification of alpha 2,6-ST from rat liver;

Weinstein, et al. *J Biol Chem* (1982) 257:13835–13844 report purification of alpha 2,3-ST which uses Gal(beta)1,3(4)GlcNAc as acceptor and/or alpha 2,6-ST which uses Gal(beta)1,4GlcNAc as acceptor, from rat liver;

Conradt, et al. "Sialic Acids" (1988) Proceedings of the Japanese-German Symposium, Berlin, p. 104 report purification of an alpha 2,3-ST from porcine liver which uses Gal(beta)1,3GalNAc as acceptor;

Sadler, et al. *J Biol Chem* (1979) 254:4434–4443; ibid 5934–5941, report purification of alpha 2,3-ST from porcine submaxilary glands, which uses beta-Gal as acceptor;

Higa, et al. *J Biol Chem* (1985) 260:8838–8849 report purification of alpha 2,6-ST from bovine submaxilary glands which uses GalNAc as acceptor; and Paulson, et al. *J Biol Chem* (1977) 252:2356–2362 report purification of alpha 2,6-ST from bovine colostrum, which uses beta-Gal as acceptor.

Of the foregoing, the enzymes prepared by Weinstein et al. and by Sadler et al. were purified to homogeneity.

A variety of techniques were used in the foregoing preparations, most commonly an affinity step which involves CDP-hexanolamine Sepharose as an affinity support. The column equilibration and elution conditions required for isolation using this kind of generalized affinity support were very critical. Furthermore, the affinity support itself is difficult to synthesize.

Recently, Sticher, et al. *Biochem J* (1988) 253:577–580 described a simple 3-step procedure for purification of Gal(beta)1,4GlcNAc-specific alpha 2,6-ST from rat liver using dichromatography on Cibacron Blue F3GA and FPLC, to purify the enzyme to apparent homogeneity. However, the absence of accompanying alpha 2,3-ST activity was not convincingly established.

Putatively pure rat liver Gal(beta)1,4GlcNAc-specific alpha 2,6-ST and porcine submaxilary gland Gal(beta) 1,3GalNAc-specific alpha 2,3-ST are commercially available; alpha 2,3-ST specific for Gal(beta)1,3GlcNAc cannot, however, be prepared easily.

Thus, although various ST enzymes have been obtained by prior art methods, there is no simple procedure for isolating a desired ST of given specificity. No previously used method has taken advantage of acceptor specificity in the design of an affinity ligand.

One acceptor of use in the present invention is Gal(beta)1,4GlcNAc (LacNAc). Elices, et al. *Arch Biochem Biophys* (1987) 254:329–341 utilized LacNAc derivatized to the commercially available Synsorb™ support beads for assay of alpha 2,3-ST and alpha 2,6-ST from rat liver. However, these supports were not used for purification of the enzymes.

Disclosure of the Invention

A simple purification procedure using synthetic oligosaccharide derivatized beads as affinity supports is employed to purify selected sialyl transferases from crude tissue extracts. The method preferably utilizes a partially purified sialyl transferase (ST) in this affinity step. The adsorption is conducted in the absence of manganous or other metal ions, but in the presence of analogs of CMP, preferably cytidine-5'-diphosphate (CDP). The affinity adsorbant comprises simple oligosaccharides such as Gal(beta)1,3GlcNAc (Le$^c$) and Gal(beta)1,4GlcNAc (LacNAc) which behave as acceptors for alpha 2,3-ST and alpha 2,6-ST respectively. The acceptor residues are derivatized to the supporting matrix, such as silica particles, preferably with covalently-linked spacer arms such as those described in U.S. Pat. Nos. 4,137,401 and 4,238,473 incorporated herein by reference.

Accordingly, in one aspect, the invention is directed to a method to isolate a first sialyl transferase of defined specificity from other sialyl transferases of alternate specificities or from other contaminating proteins, which method comprises adsorbing said first ST to an affinity support which is derivatized to an acceptor for said first sialyl transferase in the presence of a CMP analog, and in the absence of metal ions, under conditions suitable for the adsorption of said ST, followed by elution of the adsorbed ST in the absence of the CMP analog. The method is preferably conducted on a sample which is enriched in the desired ST.

DETAILED DESCRIPTION OF THE INVENTION

Figure 1:
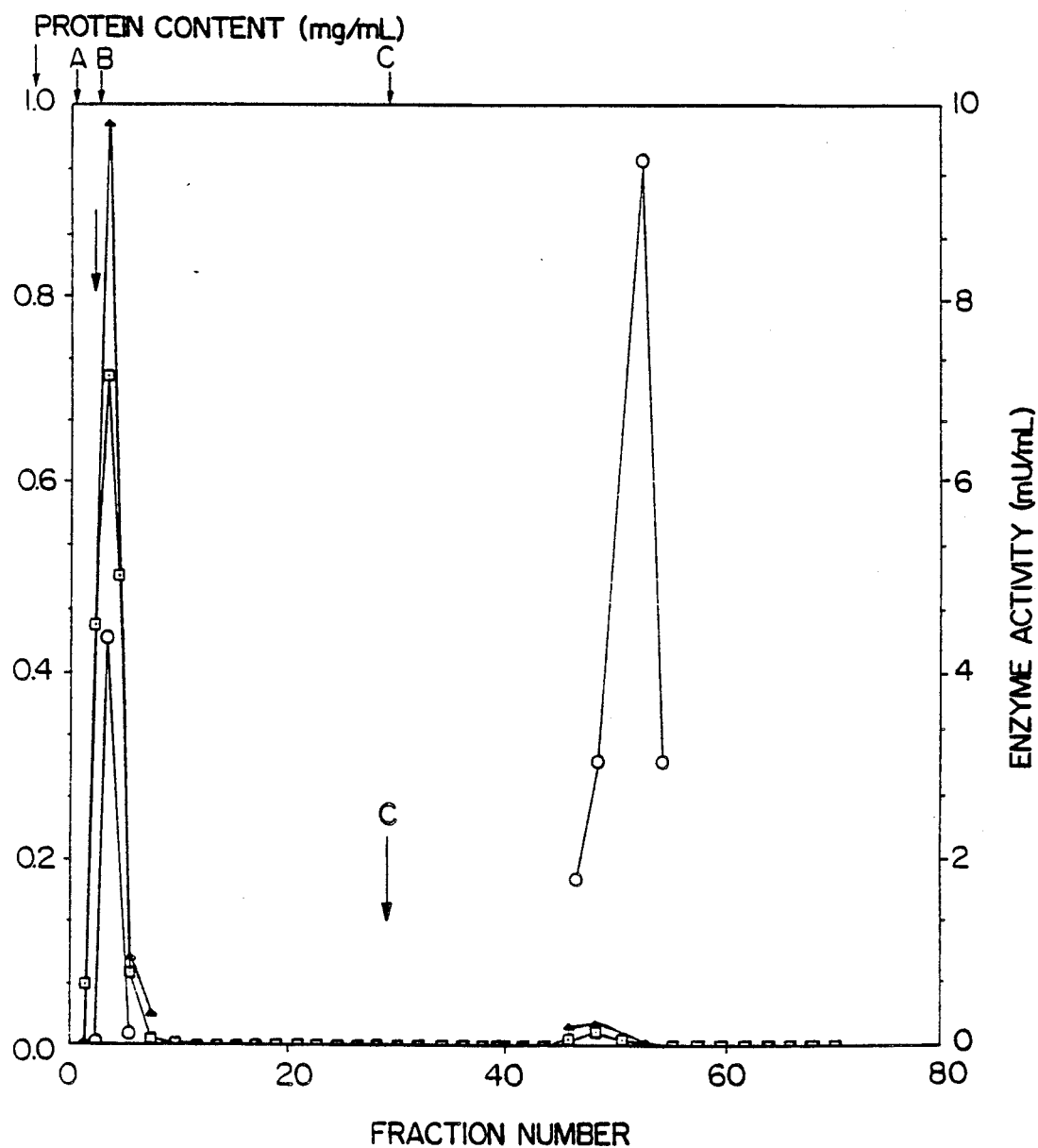
FIG. 1 shows the elution profile of alpha 2,3-ST and alpha 2,6-ST from affinity purification on Le$^c$ derivatized beads.

The invention utilizes affinity supports which are derivatized to disaccharide or oligosaccharide units representing acceptor moieties for the particular sialyl transferase to be purified. Although the invention is illustrated as set forth below with regard to alpha 2,3-ST which utilizes Le$^c$ (Gal(beta)1,3GlcNAc) as well as LacNAc as acceptor and alpha 2,6-ST which utilizes only LacNAc (Gal(beta)1,4GlcNAc) as acceptor, the approach can be used for the purification of any ST with a known acceptor specificity. Thus, for example, sialyl transferases which use beta-Gal or GalNAc as acceptors or which use Gal(beta)1,3GalNAc or Gal(beta)1,4GalNAc as acceptors, can also be purified using these corresponding acceptors or extensions thereof derivatized to support.

The invention method takes advantage of the affinity of the ST enzyme for its substrates. Thus, the desired ST will bind to its corresponding acceptor in the presence of an analog for the sialyl-CMP transferring moiety that is the additional substrate of the enzyme. Suitable analogs include cytidine-5'-diphosphate (CDP) and other modified cytidine derivatives. The acceptor is derivatized to the support through a covalently-bound spacer arm to permit accessibility for the ST to the acceptor moiety. The adsorbed ST is then eluted by use of conditions which include the absence of the CMP-sialyl analog, which conditions may be modified advantageously by addition of eluting agents suitable to the ST to be purified.

The Affinity Support

A useful approach to the construction of the affinity support is set forth in U.S. Pat. Nos. 4,137,401; 4,238,473; and 4,362,720, all incorporated herein by reference. These patents disclose the conjugation of various sugar residues to solid supports by derivatization of the reducing end of the saccharide moiety through a bridging arm, —X—CO—Y, wherein X is a spacer, preferably of the formula $(CH_2)_n$ where n is 3–19 and Y is a suitable leaving group such as —OH, —NH$_2$, —NH—NH$_2$, —N$_3$, and so forth.

Of course, modified forms of the spacer arm including heteroatoms may also be used, and a variety of solid supports may be employed for derivatization. By a solid support "derivatized" with an oligosaccharide or acceptor is meant a suitable inert support conjugated through a spacer arm (of sufficient length to provide access to the affinity ligand of an ST to be purified) to the ligand. The ligand will be a mono-, di- or trisaccharide or other extended saccharide residue which corresponds to the acceptor for which the ST is specific.

Suitable solid support materials include various silica derivatives such as silica powder, synthetic silicate such as porous glass, biogenic silicate such as diatomaceous earth, silicate-containing minerals such as kaolinite and so forth. Other suitable supports include synthetic resins or particulate polymers such as polystyrenes, polypropylenes, polysaccharides, and so forth or other commonly used chromatographic supports such as alumina. Silacious materials are particularly preferred groups, especially calcined diatomaceous earth of the cristobollite type which contain surface hydroxy. Mesh sizes vary according to intended use from about 150 to about 12.

As is well understood in the art, the solid support may need to be modified to provide reactive groups for conjugation to spacer which is in turn conjugated to the affinity ligand. For example, porous glass beads may be provided with amino groups using 3-aminopropyl triethoxysilane using the method of Weetall, H. H. et al. Method Enzymol (1974) 34b:59-72.

In an exemplary preparation, acid-washed calcined diatomite is treated with 3-aminopropyl triethoxysilane and acetone; the acetone is removed by evaporation in a vacuum and the silane-coated diatomite is washed with methanol and dried. This is coupled with the 8-azido carbonyloctyl derivative of the preferred oligosaccharide which has been prepared by treatment of the corresponding hydrazide with nitrous acid in dimethyl formamide. The conjugation is conducted in the presence of acetonitrile, which is then evaporated, and the remaining unreacted amino groups are acetylated with acetic anhydride and methanol. The methanol is removed and the product washed with water and dried overnight in an oven at 70° C. The derivatized support prepared by this method typically contains at least 0.35 umol of ligand per gram of matrix.

Included as supports, also, are materials which do not require derivatization such as agarose, cellulose, aminoethylated styrene/divinyl benzene polymers, etc. These materials can be coupled to a carboxyl derivative using a suitable linker such as di-(N-succinimidyl) carbonate (DSC) or other bis-N hydroxy succinimidyl ester, followed by reaction with an amino-terminated ligand or matrix. Coupling of amino groups via activation with a bifunctional agent such as glutaraldehyde may also be used. Amide formation using a suitable carbodiimide is an additional illustrative standard method.

In general the acceptor oligosaccharide is derivatized to the support in a range of 0.3-1 umol per gram which provides capacity for purification of 5-10 mU of ST per gram of support.

The affinity support may be further treated to obtain an integral membrane coating as described in U.S. Ser. No. 270,950, filed Nov. 9, 1988, assigned to the same assignee, and incorporated herein by reference. Briefly, the coating technique provides a coherent and ultra-thin porous polymeric film around the particles which prevents the release of fines or disintegration, while the porosity is sufficient to allow interaction between the affinity ligand and the ST to be purified. The method by which the particles are coated is described in detail in the above-referenced application and involves coating under conditions normally employed to obtain synthetic membranes such as described by Sourirajan, S., "Reverse Osmosis and Synthetic Membranes", National Research Council of Canada, Ottowa (1977). The coating may be applied before or after the introduction of the affinity ligand. Affinity supports containing such coatings are commercially available under the trademark Synsorb TM (Chembiomed, Edmonton, Alberta, Canada).

Sample Preparation

The sample containing the mixture of sialyl transferases to be purified is preferably initially concentrated and enriched in the desired ST prior to final purification using the method of the invention. Direct use of the affinity method as applied to crude extracts without prior purification is possible, but disadvantageous due to the low concentration of STs in such extracts. Accordingly, some concentration of the ST in the sample is helpful, and, if possible, enrichment in the desired species is advantageous.

Methods to effect such concentration and enrichment are known in the art. An exemplary procedure is set forth by Sticher, et al. *Biochem J* (1988) 253:577–580, incorporated herein by reference. This method employs dye chromatography on Cibacron Blue F3GA-Sepharose 6B.

Briefly, Cibacron Blue F3GA is covalently attached to sepharose 6B using the triazine coupling method of Dean, FDG, et al. *J Chromatog* (1979) 165:301–319. Sepharose 6B is suspended in water and a solution of Cibacron Blue F3GA is added; the mixture is treated with sodium chloride and then with base. The mixture is then incubated for three days at 40° C., filtered and washed with water, 1M NaCl, 4–6M urea and water. Typically the adsorbant contains 2–4 umol dye per gram gel.

The desired sialyl transferases are extracted from various tissues, e.g., rat or porcine liver, porcine or bovine submaxilary gland, bovine colostrum, etc., using a non-ionic detergent as set forth by Weinstein, et al. *J Biol Chem* (1982) 257:13835–13844, incorporated herein by reference. The extraction is conducted using sodium cacodylate buffer, pH 6 in the presence of manganous ion and non-ionic detergent such as Triton X-100, Nonidet P-40, and preferably Triton CF-54.

The detergent extracts are then neutralized with EDTA to remove $Mn^{+2}$ and concentrated on the Cibacron Blue-Sepharose column. An initial concentration is accomplished by adsorption onto the dye support followed by elution with a 2M NaCl pulse. After desalting, the concentrate is applied to a second Cibacron Blue-Sepharose column and separated into fractions enriched in the desired sialyl transferases. For extracts of rat liver, high concentrations of alpha 2,3-ST specific for the acceptor $Le^c$ (or LacNAc) and alpha 2,6-ST specific for LacNAc are obtained.

After application to the second column, an initial elution at pH 4.8 (in the presence of 2M salt) provides a fraction enriched in the alpha 2,6-ST; a second fraction eluted at pH 6.5 (in 2M NaCl) is enriched in alpha 2,3-ST. The ST-containing fractions are then prepared for use in the affinity method of the invention by dialysis, and can be stored at −20° C. in a buffer containing 50% glycerol.

The foregoing method to obtain concentrated and enriched fractions is exemplary, and other concentration and enrichment methods can also be used.

The Method

The solid support derivatized to acceptor moiety, preferably in the form of beads, is extensively washed and equilibrated with a suitable buffer, such as sodium cacodylate at a suitable pH wherein the buffer contains 1–5 mM of the CMP-sialic acid analog, such as CDP. The sample, enriched in the partially purified ST and dissolved in the same analog-containing buffer, is applied to the derivatized support for sufficient time to accomplish adsorption. An equilibration time of 1–2 hrs is required. If the derivatized support is contained in a column, low flow rates of 2–6 ml/hr are needed. The ST specific for the acceptor ligand is absorbed to the column, while contaminating ST and other proteins are not adsorbed. The adsorbed ST is then eluted from the support using buffer free of the CMP-sialic acid analog; elution may be aided by salt or appropriate competitive oligosaccharides, such as lactose in the case of $Le^c$ columns.

Assay for ST-containing Fractions

The presence of ST in the eluates (or other samples) can be assayed using standard procedures as described by Paulson, et al. *J Biol Chem* (1977) 252:2363–2371 and by Weinstein, et al. *J Biol Chem* (1982) 257:13835–13844. The assay (60 ul volume) contains acceptor substrate appropriate to the ST to be assayed. Suitable concentrations are, for example, lacto-N-tetraose, 10 ug; $Le^c$, 2 mM; and LacNAc, 2 mM. Suitable amounts of enzyme are (0–0.2 mU). Other components include 50 ug bovine serum albumin (BSA) and 9 nmol CMP-14C-sialic acid (about 5000 cpm/nmol) in 50 mM sodium cacodylate, pH 6.0 with 0.5% Triton CF-54. The reaction mixtures are incubated at 37° C. for 15–60 min, and the radioactive product is isolated and quantitated on Pasteur pipette columns of Dowex 1-X8 (phosphate, 100–200 mesh). One unit of activity is defined as 1 umol product formed per minute of incubation at saturating substrate concentrations. Protein concentrations are measured using the commercially available Bio Rad assay, using BSA as standard.

The following examples are intended to illustrate but not to limit the invention. Example 1 describes the preparation of samples from rat liver to obtain enriched and concentrated alpha 2,3-ST and alpha 2,6-ST for application in the method of the invention.

Example 2 is a control showing that adsorption to affinity support does not occur in the presence of CMP and manganous ion.

Example 3 illustrates the purification of alpha 2,3-ST using $Le^c$ derivatized support in the presence of CDP; Example 4 illustrates an improved elution procedure in the protocol of Example 3 using lactose; Example 5 illustrates a different acceptor concentration on the support.

Example 6 illustrates the purification of alpha 2,6-ST using LacNAc derivatized support.

Figure 4:
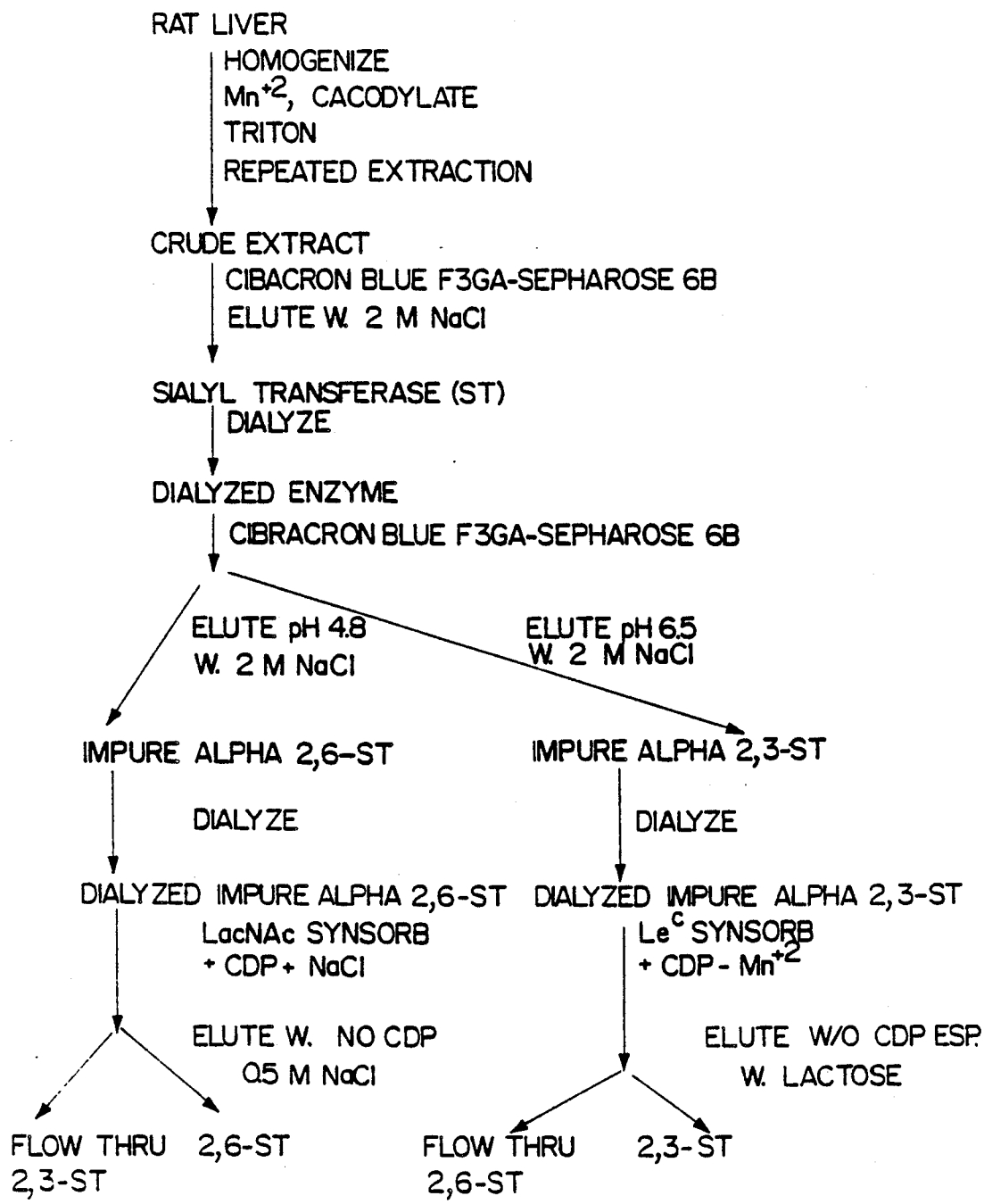
FIG. 4 is a flow diagram showing a preferred protocol for the isolation of alpha 2,6-ST which uses LacNAc as an acceptor and for purification of alpha 2,3-ST which utilizes Le$^c$ as an acceptor.

The figures referred to in the Examples are described in detail following Example 6. The last included figure, FIG. 4, is an outline of the exemplified procedures in flow chart form.

EXAMPLE 1

Partial Purification of α2,3- and α,2,6-Sialyltransferases from Rat Liver

All preparative procedures are performed at 4° C. Glass columns and other glassware are siliconized before use with Prosil®-28 (PCR Incorporated).

Frozen rat livers (195 g) are thawed, rinsed with distilled water, grounded, and then homogenized in a Cuisinart blender (four 10 s bursts with 30 s rest intervals) with 1 L of 25 mM sodium cocodylate (pH 6.0), 20 mM $MnCl_2$ (buffer A). The homogenate is centrifuged at 7,000× g for 1 h, and the resulting pellet is suspended in 0.6 L of buffer A by homogenization (two 10 s bursts) and centrifuged as above. Washed pellets are resuspended in 0.6 L of 25 mM sodium cacodylate (pH 6.0), 10 mM $MnCl_2$ (buffer B) by homogenization (two 10 s bursts) and a solution of Triton CF-54 is added to a final concentration of 1.4% (w/v). After stirring for 45 min, the suspension is centrifuged as before. The supernatant is decanted, filtered through glass wool, and the $Mn^{2+}$ (used in the extraction buffer) is titrated with 0.5M EDTA (pH 7.7) while maintaining the pH at 6.0 by dropwise addition of 5N NaOH. The detergent extraction is repeated twice with the pellets by using the same procedure as above, and the supernatants thus obtained are combined with the first extract after EDTA treatment.

The crude extract (1.6 L, 3.5 mg protein/mL) is applied at a flow rate of 240 mL/h to a column (5×17 cm) of Cibacron Blue F3GA-Sepharose 6B (prepared according to Dean and Watson, 1979) equilibrated in 10 mM sodium cacodylate (pH 6.5), 0.15M NaCl, 25% glycerol, 0.1% Triton CF-54 (buffer C) in two portions, with a wash step in between with buffer C. The column is washed extensively with ~4 L of buffer C to remove inert protein, and the adsorbed sialyltransferases are eluted with buffer C containing 2.0M NaCl. Active fractions containing sialyltransferase are pooled (90 mL, 4.5 mg protein/mL) and dialyzed against 2×2 L of buffer C. The dialyzed enzyme is applied to a second dye column (1.5×15 cm) pre-equilibrated with buffer C at a flow rate of 30 mL/h. The column is washed with 500 mL of buffer C followed by 200 mL of 50 mM sodium cacodylate, pH 4.8, 0.15M NaCl, 25% glycerol, 0.1% Triton CF-54 (buffer D). The column is then eluted with buffer D containing 2.0M NaCl, and the active fractions which contain mainly α2,6-sialyltransferase are pooled (22 mL, 1.2 mg protein/mL, approximately 384 mU of α2,6-sialyltransferase and 53 mU of α2,3-sialyltransferase based on assays using LacNAc and lacto-N-tetraose as the acceptor substrates, respectively) and dialyzed against 2×1.5 L of buffer C. The column is re-equilibrated with 500 mL of buffer C, and the remainder of the adsorbed enzymes which is rich in α2,3-sialyltransferase is eluted from the column with buffer C containing 2.0M NaCl. The second active fractions are pooled together (18 mL, 0.9 mg protein/mL, 245 mU of α2,3-sialyltransferase and 55 mU of α2,6-sialyltransferase), and dialyzed as above. Both dialyzed enzyme fractions are adjusted to 50% glycerol and stored at −20° C. until final purification by affinity chromatography as described in Examples 2-6.

EXAMPLE 2

Affinity Purification of Rat Liver α2,3-Sialyltransferase on Le$^c$-SYNSORB Beads using Cytidine 5'-monophosphate (CMP) and Manganese Chloride ($MnCl_2$) for Reversible Binding About 2 g of Le$^c$-SYNSORB beads (0.48 μmol of oligosaccharide g of beads) are washed with water, degassed under vacuum for 10–15 min, and packed into a column (1.4×2.5 cm). The column is equilibrated with 10 mM sodium cacodylate (pH 6.5), 0.15M NaCl, 1 mM CMP, 5 mM $MnCl_2$, 25% glycerol, 0.1% Triton CF-54 (buffer I), and is kept at 4° C. throughout the procedure.

A pooled fraction (2 mL, 5 mg protein) containing α2,3-sialyltransferase (~75 mU) and α2,6-sialyltransferase (~18 mU), partially purified from rat liver as described in Example 1, is diluted with equal volume of buffer 1 containing 2 mM CMP and then applied to the column at a flow rate of 4.0 mL/h. After allowing the enzyme to interact with the beads for about 2 h, the column is washed with ~50 mL of 10 mM sodium cacodylate (pH 6.5), 0.5M NaCl, 1 mM CMP, 5 mM $MnCl_2$, 25% glycerol, 0.1% Triton CF-54 (buffer II) to remove any loosely bound proteins. Finally, the column is eluted with 10 mM sodium cacodylate (pH 6.5), 0.5M NaCl, 25% glycerol, 0.1% Triton CF-54 (buffer III). Protein estimation and also the enzyme activity determination shows that most of the α2,3-sialyltransferase elutes unretarded with the contaminating α2,6-sialyltransferase and inert protein in the flow-through volume and subsequent wash step. This indicates that the α2,3-sialyltransferase does not efficiently bind to the Le$^c$-SYNSORB column in presence of CMP and $MnCl_2$.

EXAMPLE 3

Affinity Purification of Rat Liver α2,3-Sialyltransferase on Le$^c$-SYNSORB Beads using Cytidine 5'-diphosphate (CDP) for Reversible Binding The same purification procedure as in Example 2 is carried out except that only CDP (1 mM) is used instead of CMP (1 mM) and $MnCl_2$ (5 mM) is omitted in both buffers I and II. The size of the Le$^c$-SYNSORB (0.48 μmol of oligosaccharide/g of beads) column and the amount of partially purified α2,3-sialyltransferase applied to the column are about the same as in Example 2. Fractions eluting from the column are assayed for protein content and enzyme activity. The results are presented in FIG. 1 which shows that α2,3-sialyltransferase adsorbs strongly to the column during application and subsequent wash steps, while bulk of the inert protein and α2,6-sialyltransferase elute only slightly retarded. The α2,3-sialyltransferase elutes upon omission of CDP from the column buffer.

The active fractions containing α2,3-sialyltransferase (~35 mU, ~0.04 mg protein) with undetectable α2,6-sialyltransferase are pooled, and dialyzed against 100 bed volumes of 50 mM sodium cacodylate (pH 6.0), 0.3M NaCl, 50% glycerol, 0.1% Triton CF-54 (buffer IV) for 48 h with a change of buffer after 24 h before storage at −20° C. This procedure yields α2,3-sialyltransferase with ~47% recovery of the total enzyme activity applied to the column. It represents about 60-fold purification by the Le$^c$-SYNSORB beads, and roughly 20,000-fold purification of the α2,3-sialyltransferase over the activity present in the tissue homogenate, while there is a complete separation from the contaminating α2,6-sialyltransferase activity.

EXAMPLE 4

Affinity Purification of Rat Liver α2,3-sialyltransferase on Le$^c$-SYNSORB Beads using Cytidine 5'-diphosphate (CDP) for Reversible Binding and Lactose to Facilitate Elution The same purification procedure as in Example 3 is carried out with the following exceptions: (a) 5 mM (instead of 1 mM) CDP is used in buffer I and II, (b) lactose (0.2M) is added to buffer III, and (c) about 85 mU of α2,3-sialyltransferase and 18 mU of α2,6-sialyltransferase activity (~6 mg total protein), partially purified as in Example 1, is applied to a column (1.4×14 cm) of Le$^c$-SYNSORB beads (~10 g) containing 0.48 μmol of oligosaccharide per g of beads after dilution with equal volume of buffer I containing 10 mM CDP. The elution profile is shown in FIG. 2 which indicates that α2,3-sialyltransferase is adsorbed almost quantitatively to the Le$^c$-SYNSORB column during application and subsequent wash steps. Also, the adsorbed α2,3-sialyltransferase elutes in a very sharp peak upon inclusion of lactose, an alternate acceptor substrate, in buffer III which when compared to FIG. 1 (Example 3) suggests that lactose facilitates the elution of the enzyme.

About 60 mU of purified α2,3-sialyltransferase (~0.08 mg protein) is obtained from this procedure which accounts for 71% recovery of the total enzyme activity applied to the column. This represents about 55-fold purification of the α2,3-sialyltransferase by the Le$^c$-SYNSORB beads with a complete separation from the contaminating α2,6-sialyltransferase, and roughly 17,000-fold purification of the α2,3-sialyltransferase activity over that present in the tissue homogenate. The purified enzyme is dialyzed against buffer IV as in Example 3, and stored at −20° C.

EXAMPLE 5

Affinity Purification of Rat Liver α2,3-sialyltransferase on Le$^c$-SYNSORB Beads (with Higher Oligosaccharide Density) using CDP for Reversible Binding and Lactose to Facilitate Elution The same purification procedure as in Example 4 is carried out except that the partially purified α2,3-sialyltransferase (85 mU) is applied to a column (1.4×7 cm) of Le$^c$-SYNSORB beads (~5 g) containing 1.10 μmole of oligosaccharide/g of beads. About 27 mU of α2,3-sialyltransferase (~0.01 mg protein) which represents approximately 200-fold purification by the Le$^c$-SYNSORB beads (about 60,000-fold over the activity in tissue homogenate), again with a complete separation from the α2,6-sialyltransferase, is obtained from the fractions eluted in presence of lactose (no CDP). This corresponds only to 31% recovery from the column of the total amount of enzyme activity applied in contrast to 71% recovery in Example 4. However, the lower recovery is due to insufficient amount of the affinity adsorbent (5 g vs 10 g used in Example 4) in the column which means a higher oligosaccharide concentration in the beads is not necessarily useful with respect to increased binding of the enzyme, possibly due to steric and/or diffusional restrictions.

Comparison with results in Example 4 indicate that a maximum of 6 to 8 mU of the enzyme could be bound per g of the affinity adsorbent provided of course the ligand density is sufficiently high, i.e. approximately 0.5 μmole/g to saturate with the enzyme. It is to be noted that the actual capacity or efficiency of the column would depend on other characteristics of the adsorbent, viz. the particle size as well as the porosity of the beads or on such column operating conditions as the loading or incubation time, elution rate, temperature, etc.

EXAMPLE 6

Affinity Purification of Rat Liver α2,6-Sialyltransferase on LacNAc-SYNSORB Beads using CDP for Reversible Binding The same purification procedure as in Example 4 is carried out except that about 75 mU (based on assay using LacNAc as acceptor substrate) of α2,6-sialyltransferase and 10 mU of α2,3-sialyltransferase (~5 mg protein), partially purified as in Example 1, is applied to a column (1.4×14 cm) of LacNAc-SYNSORB beads (~10 g; 0.70 μmol of oligosaccharide/g of beads) equilibrated with buffer I which contains 5 mM CDP and 0.15M NaCl. The elution profile of the column (shown in FIG. 3) indicates that α2,6-sialyltransferase adsorbs almost quantitively to the column during application, while the contaminating α2,3-sialyltransferase elutes unretarded with buffer I, i.e. in flow-through volume. However, unlike the α2,3-sialyltransferase (Examples 2–5), the adsorbed α2,6-sialyltransferase elutes from the column with the bulk of the protein during the wash step with buffer II containing high salt (0.5M NaCl) as well as CDP (5 mM). This suggests that even in the presence of CDP the interaction between LacNAc-beads and the α2,6-sialyltransferase is reversed by the higher salt concentration.

In a separate experiment, the above purification procedure is repeated except that about 22 mU of partially purified α2,6-sialyltransferase and 3 mU of α2,3-sialyltransferase (~1.5 mg protein) is applied to a column of the same LacNAc-SYNSORB beads (~2 g) followed by a wash step with buffer I which removes the bulk of the protein as well as the contaminating α2,3-sialyltransferase. About 10 mU of the α2,6-sialyltransferase (~0.03 mg protein) is now eluted (23-fold purification by the LacNAc-SYNSORB beads) with an undetectable amount of the contaminating α2,3-sialyltransferase after direct application of buffer III containing 0.5M NaCl but no CDP, which accounts for 45% recovery of the total enzyme activity applied. This low recovery is possibly due to insufficient quantities of the affinity adsorbent, and is consistent with that obtained in Example 5.

FIGURE LEGENDS

Figure 2:
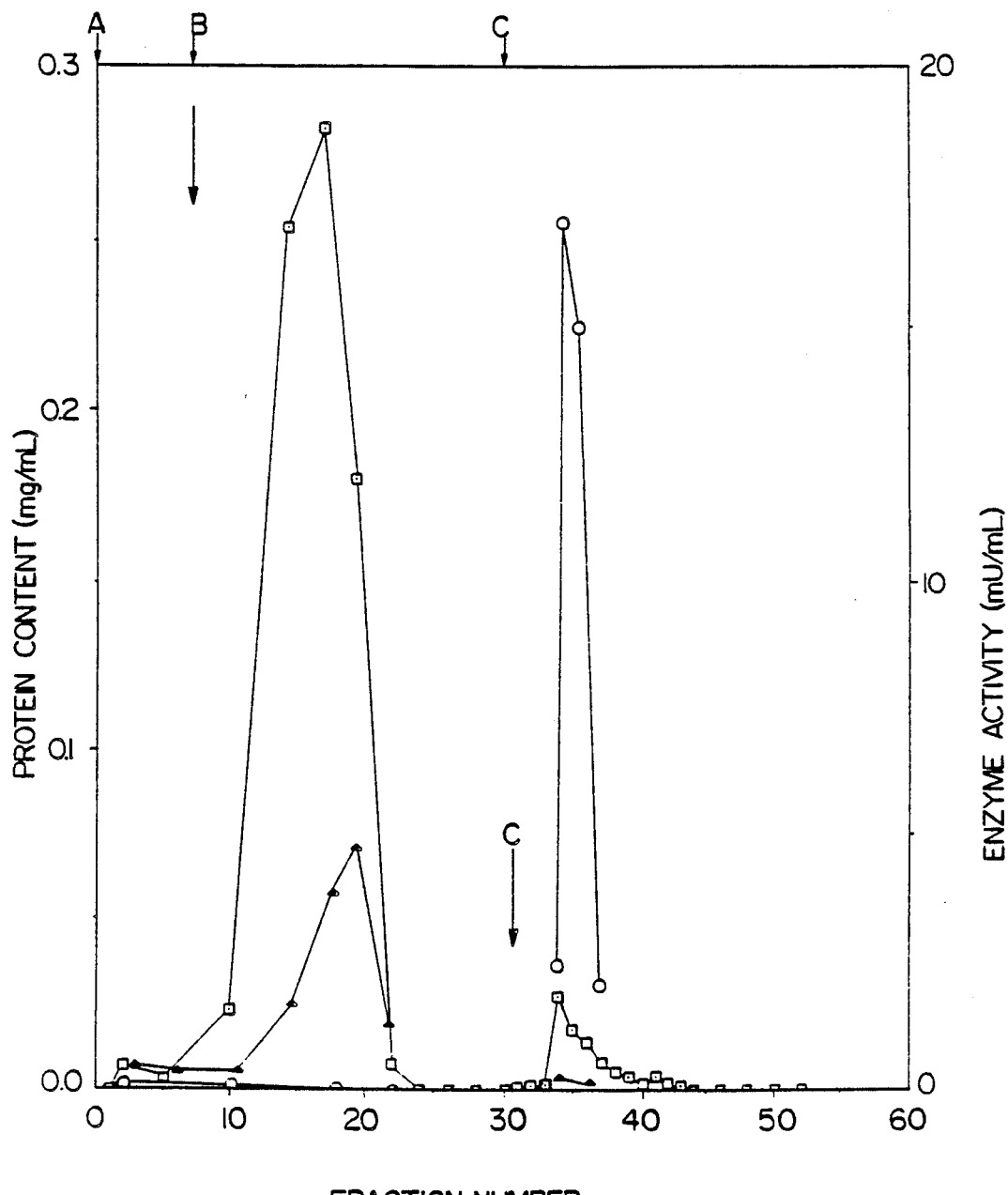
FIG. 2 shows the elution profile of alpha 2,3-ST and alpha 2,6-ST from affinity purification on Le$^c$ derivatized beads with the addition of lactose as an eluting agent.

FIG. 1 shows the elution profile (2.1 mL fractions) of total protein (□) as well as the α2,3-sialyltransferase (○) and α2,6-sialyltransferase activities (▲) from affinity purification of rat liver α2,3-sialyltransferase on Le$^c$-SYNSORB beads (2 g, 0.48 μmole/g) using cytidine 5'-diphosphate (CDP, 1 mM) for reversible binding (Example 3). The application of various buffers to the affinity column (1.4×2.5 cm) are as indicated: (A) Buffer I containing 10 mM sodium cacodylate (pH 6.5), 0.15M NaCl, 1 mM CDP, 25% glycerol and 0.1% Triton CF-54; (B) Buffer II, same as I except that the concentration of NaCl is increased to 0.5M; (C) Buffer III, same as II except that CDP is omitted.

FIG. 2 shows the elution profile (2.2 mL fractions) of total protein (□) as well as the α2,3-sialyltransferase (○) and α2,6-sialyltransferase activities (▲) from affinity purification of rat liver α2,3-sialyltransferase on Le$^c$-SYNSORB beads (10 g, 0.48 μmole/g) using cytidine 5'-diphosphate (CDP, 5 mM) for reversible binding and lactose (0.2M) to facilitate elution (Example 4). The application of various buffers to the affinity column (1.4×14 cm) are as indicated: (A) Buffer I containing 10 mM sodium cacodylate (pH 6.5), 0.15M NaCl, 5 mM CDP, 25% glycerol and 0.1% Triton CF-54; (B) Buffer II, same as I except that 0.5M NaCl is used; (C) Buffer III, same as II except that CDP is omitted and 0.2M lactose is added.

Figure 3:
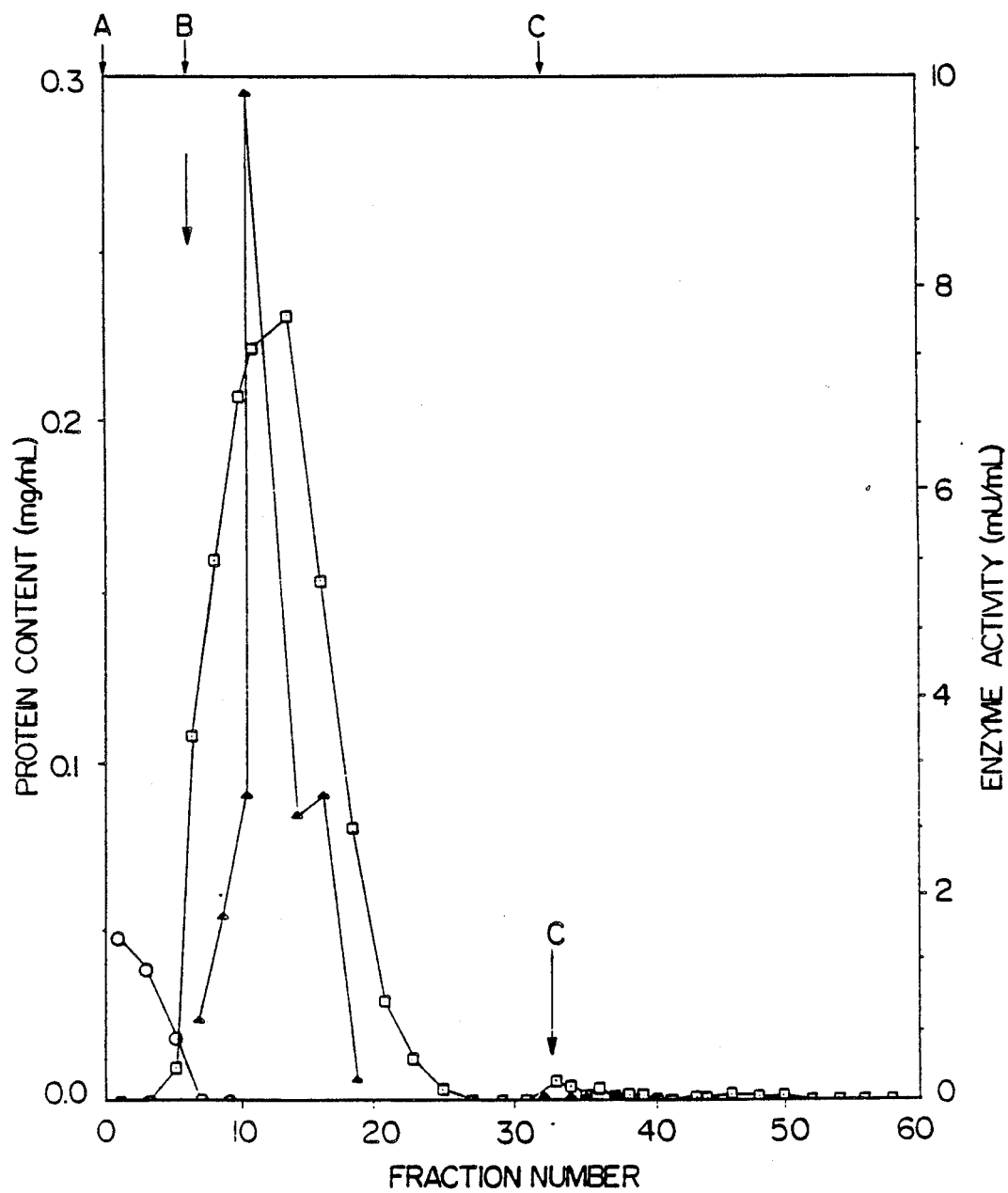
FIG. 3 shows the elution profile of alpha 2,3-ST and alpha 2,6-ST from affinity purification using LacNAc derivatized beads.

FIG. 3 shows the elution profile (2.0 mL fractions) of total protein (□) as well as the α2,3-sialyltransferase () and α2,6-sialyltransferase (▲) activities from affinity purification of rat liver α2,6-sialyltransferase on LacNAc-SYNSORB beads (10 g, 0.7 μmole/g) using cytidine 5'-diphosphate (CDP, 5 mM) for binding of the enzyme to the adsorbent (Example 6). The application of different buffers to the affinity column (1.4×14 cm) are as indicated: (A) Buffer I containing 10 mM sodium cacodylate (pH 6.5), 0.15M NaCl, 5 mM CDP, 25% glycerol and 0.1% Triton CF-54; (B) Buffer II, same as I except that the concentration of NaCl is increased to 0.5M; (C) Buffer III, same as II except that CDP is omitted.

We claim:

1. A method to purify a first sialyl transferase (ST) which catalyses sialylation of a known specific acceptor from a second ST which catalyses sialylation of a different known specific acceptor and/or from other protein contaminants, which method comprises:

contacting a sample containing the said first ST with a chromatographic support derivatized through a covalently bound spacer arm to said specific known acceptor in the presence of cytidine-5'-diphosphate (CDP) under conditions wherein said first ST is adsorbed; and eluting the adsorbed first ST in the absence of said CDP.

2. The method of claim 1 wherein the first ST is an alpha 2,3-sialyl transferase and the acceptor is Gal(beta)1,3GlcNAc.

3. The method of claim 2 wherein the chromatographic support derivatized to acceptor is silica matrix derivatized to Gal(beta)1,3GlcNAc with a covalently bound spacer arm.

4. The method of claim 2 wherein the first ST is eluted from the support in the presence of lactose.

5. The method of claim 2 wherein said sample is prepared by eluting sialyl transferases from a Cibacron Blue F3GA-Sepharose 6B column with pH 6.5 buffer in the presence of 2M NaCl.

6. The method of claim 1 wherein the first ST is an α2,6-sialyl transferase and the acceptor is Gal($\beta$)1,4GlcNAc.

7. The method of claim 6 wherein the chromatographic support derivatized to acceptor is silica matrix derivatized to Gal($\beta$)1,4GlcNAc with covalently-bound spacer arm.

8. The method of claim 6 wherein the first ST is eluted from the support in the presence of salt.

9. The method of claim 6 wherein said sample is prepared by eluting sialyl transferases from a Cibacron Blue F3GA-Sepharose 6B column with pH 6.5 buffer in the presence of 2M NaCl.

* * * * *